(12) United States Patent
Sakamoto et al.

(10) Patent No.: US 8,680,330 B2
(45) Date of Patent: Mar. 25, 2014

(54) PROCESS FOR PRODUCING (METH) ACRYLIC ACID

(75) Inventors: Kazuhiko Sakamoto, Himeji (JP); Koji Ueno, Himeji (JP); Yoshitake Ishii, Himeji (JP); Takashi Sugimoto, Himeji (JP); Masatsugu Kitaura, Himeji (JP); Satoshi Nakagawa, Himeji (JP); Kunihiko Suzuki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 238 days.

(21) Appl. No.: 13/147,643

(22) PCT Filed: Jan. 29, 2010

(86) PCT No.: PCT/JP2010/051261
§ 371 (c)(1),
(2), (4) Date: Aug. 3, 2011

(87) PCT Pub. No.: WO2010/090143
PCT Pub. Date: Aug. 12, 2010

(65) Prior Publication Data
US 2011/0319661 A1    Dec. 29, 2011

(30) Foreign Application Priority Data

Feb. 3, 2009 (JP) ................................ 2009-022475
Jun. 25, 2009 (JP) ................................ 2009-151293

(51) Int. Cl.
*C07C 51/42* (2006.01)
(52) U.S. Cl.
USPC ....................................................... 562/600
(58) Field of Classification Search
None
See application file for complete search history.

(56) References Cited

U.S. PATENT DOCUMENTS

| 3,621,664 A | 11/1971 | Saxer |
| RE32,241 E | 9/1986 | Saxer |
| 5,326,916 A | 7/1994 | Kobayashi et al. |

(Continued)

FOREIGN PATENT DOCUMENTS

| EP | 0 648 520 | 4/1995 |
| JP | 53-41637 | 11/1978 |

(Continued)

OTHER PUBLICATIONS

Chinese Office Action issued Apr. 2, 2013 in corresponding Chinese Application No. 201080004971.3, with English translation thereof.

(Continued)

*Primary Examiner* — Karl J Puttlitz
(74) *Attorney, Agent, or Firm* — Wenderoth, Lind & Ponack, L.L.P.

(57) ABSTRACT

A process for producing (meth)acrylic acid of the present invention comprises the steps in the following order: a crystallization step of supplying a cooling medium cooled by a heat source device to a crystallizer to obtain a (meth)acrylic acid crystal from a crude (meth)acrylic acid solution; an adjustment step of returning the cooling medium discharged from the crystallizer to the crystallizer without cooling; a sweating step of supplying a heating medium to the crystallizer to partially melt the (meth)acrylic acid crystal, thereby obtaining a melted liquid, and discharging the melted liquid from the crystallizer; and a melting step of supplying the heating medium to the crystallizer to melt the (meth)acrylic acid crystal, thereby obtaining purified (meth)acrylic acid. According to the present invention, purified (meth)acrylic acid with high purity can be obtained.

19 Claims, 1 Drawing Sheet

(56) References Cited

U.S. PATENT DOCUMENTS

| | | | |
|---|---|---|---|
| 5,523,480 A | 6/1996 | Bauer, Jr. et al. | |
| 5,817,865 A | 10/1998 | Machhammer et al. | |
| 5,935,534 A * | 8/1999 | Umino et al. | 422/245.1 |
| 6,541,665 B1 | 4/2003 | Bastiaensen et al. | |
| 7,183,428 B2 | 2/2007 | Ueno et al. | |
| 2004/0249199 A1 | 12/2004 | Ueno et al. | |
| 2005/0222459 A1* | 10/2005 | Nordhoff et al. | 562/600 |
| 2006/0237356 A1* | 10/2006 | Heilek et al. | 210/323.2 |
| 2008/0071111 A1 | 3/2008 | Nakagawa | |

FOREIGN PATENT DOCUMENTS

| | | |
|---|---|---|
| JP | 5-246927 | 9/1993 |
| JP | 7-278045 | 10/1995 |
| JP | 8-281002 | 10/1996 |
| JP | 9-155101 | 6/1997 |
| JP | 9-227445 | 9/1997 |
| JP | 10-156102 | 6/1998 |
| JP | 2002-519402 | 7/2002 |
| JP | 2003-126607 | 5/2003 |
| JP | 2005-15478 | 1/2005 |
| JP | 2008-74759 | 4/2008 |
| WO | 2008/114745 | 9/2008 |

OTHER PUBLICATIONS

Supplementary European Search Report issued Nov. 25, 2013 in European Application No. 10738477.8.

Office Action issued Dec. 3, 2013 in Japanese Application No. 2009-151293, with English translation thereof.

* cited by examiner

PROCESS FOR PRODUCING (METH) ACRYLIC ACID

TECHNICAL FIELD

The present invention relates to a process for producing (meth)acrylic acid by a crystallization operation.

BACKGROUND ART

Conventionally, it is known a process for industrially producing (meth)acrylic acid by gas-phase catalytic oxidation of a (meth)acrylic acid production raw material. (Meth)acrylic acid-containing gas generated by gas-phase catalytic oxidation of the (meth)acrylic acid production raw material is, for example, collected by a liquid medium to be recovered as a crude (meth)acrylic acid solution, and then, the crude (meth) acrylic acid solution is purified by methods such as distillation, diffusion, extraction, crystallization, or the like.

For purifying crude (meth)acrylic acid by crystallization, it is generally known that a dynamic crystallization apparatus or a static crystallization apparatus is employed, for example. As a method for purifying a crude methacrylic acid solution by crystallization, Patent Literature 1 discloses a method of crystallizing and melting of a crude methacrylic acid solution to purify, for example. In Patent Literature 1, melting is performed in twice, and the melt obtained by the first melting (a sweating step) is discharged from the system and the melt obtained by the second melting is recovered as purified methacrylic acid. Patent Literature 2 discloses a dynamic crystallization apparatus having a plurality of projections on a surface on which a crystal is formed in order to prevent dropping of the crystal at the time of crystallization and quickly melt the crystal. Patent Literature 3 discloses a method for carrying out crystallization of acrylic acid using a crystallization apparatus equipped with a scraping means, in which melted acrylic acid mixed with a polymerization inhibitor is circulated and supplied to a crystal in order to prevent polymerization of purified acrylic acid.

CITATION LIST

Patent Literature

Patent Literature 1
Japanese Unexamined Laid-open Patent Application Publication No. 7-278045
Patent Literature 2
Japanese Unexamined Laid-open Patent Application Publication No. 8-281002
Patent Literature 3
Japanese Unexamined Laid-open Patent Application Publication No. 9-155101

SUMMARY OF INVENTION

Technical Problem

In the methods disclosed in Patent Literatures 1 to 3, purified (meth)acrylic acid is produced from a crude (meth) acrylic acid solution by a crystallization step, a sweating step and a melting step. However, the purified (meth)acrylic acid obtained by these methods includes a small amount of impurities though it is purified. Therefore, thus obtaining purified (meth)acrylic acid with higher purity is further desired.

The present invention has been achieved in view of the above circumstances, and the object of the present invention is to provide a process for producing (meth)acrylic acid that can obtain purified (meth)acrylic acid with higher purity.

Solution to Problem

According to the present invention, it has been found that in the process for producing (meth)acrylic acid including a crystallization step, a sweating step and a melting step, purified (meth)acrylic acid with higher purity can be obtained by providing an adjustment step of returning a cooling medium discharged from a crystallizer to the crystallizer without cooling prior to the sweating step. Thus, a process for producing (meth)acrylic acid of the present invention which solves the above problems comprises the steps in the following order: a crystallization step of supplying a cooling medium cooled by a heat source device to a crystallizer to obtain a (meth)acrylic acid crystal from a crude (meth)acrylic acid solution; an adjustment step of returning the cooling medium discharged from the crystallizer to the crystallizer without cooling; a sweating step of supplying a heating medium to the crystallizer to partially melt the (meth)acrylic acid crystal, thereby obtaining a melted liquid, and discharging the melted liquid from the crystallizer; and a melting step of supplying the heating medium to the crystallizer to melt the (meth)acrylic acid crystal, thereby obtaining purified (meth)acrylic acid.

By providing the adjustment step, temperatures of the cooling medium at the outlet and inlet of the crystallizer are made uniform, and temperature of the cooling medium in the crystallizer is also made uniform. As a result, temperature of the (meth)acrylic acid crystal in the crystallizer is made uniform. Therefore, according to the present invention, the (meth) acrylic acid crystal can be uniformly partially-melted in the subsequent sweating step, whereby impurities presented between the crystal or on the surface of the crystal are efficiently removed, and in the melting step, purified (meth) acrylic acid with higher purity is obtained.

In the adjustment step, it is preferred that the cooling medium discharged from the crystallizer is returned to the crystallizer without passing through the heat source device. Thereby, it becomes possible to decrease temperature variation of the cooling medium after discharged from the crystallizer and until returned to the crystallizer.

The adjustment step preferably takes 1 minute or longer and 10 minutes or shorter. When the adjustment step takes 1 minute or longer, the temperature of the cooling medium in the crystallizer is made uniform sufficiently. When the adjustment step takes 10 minutes or shorter, (meth)acrylic acid can be produced without causing much lowering of productivity.

In the adjustment step, the temperature variation of the cooling medium after discharged from the crystallizer and until returned to the crystallizer is preferably within 1.0° C. When the temperature variation is within 1.0° C., the temperature of the cooling medium in the crystallizer is made uniform sufficiently, whereby the purified (meth)acrylic acid with higher purity can be easily obtained finally.

It is preferable that the process of the present invention is for producing acrylic acid and the acrylic acid crystal is melted in the melting step so that temperature of the purified acrylic acid is in the range of 18° C. to 25° C. and temperature difference between the heating medium and the purified acrylic acid is in the range of 5° C. to 25° C. When the melting step is conducted while controlling the temperatures of the purified (meth)acrylic acid and the heating medium in these ranges, melting speed of the acrylic acid crystal is increased, resulting in improving productivity of acrylic acid.

It is preferred that the acrylic acid crystal is melted while being wetted with the purified acrylic acid. In addition, it is also preferred that the purified acrylic acid is circulated through the crystallizer to melt the acrylic acid crystal. When the acrylic acid crystal is melted in this manner, the acrylic acid crystal can be more efficiently melted.

Advantageous Effects of Invention

According to the process for producing (meth)acrylic acid of the present invention, purified (meth)acrylic acid with higher purity can be obtained.

DESCRIPTION OF THE PREFERRED EMBODIMENTS

A process for producing (meth)acrylic acid of the present invention comprises the steps of: a crystallization step of supplying a cooling medium cooled by a heat source device to a crystallizer to obtain a (meth)acrylic acid crystal from a crude (meth)acrylic acid solution; an adjustment step of returning the cooling medium discharged from the crystallizer to the crystallizer without cooling; a sweating step of supplying a heating medium to the crystallizer to partially melt the (meth)acrylic acid crystal, thereby obtaining a melted liquid, and discharging the melted liquid from the crystallizer; and a melting step of supplying the heating medium to the crystallizer to melt the (meth)acrylic acid crystal, thereby obtaining purified (meth)acrylic acid. In the present invention, purified (meth)acrylic acid is obtained from a crude (meth)acrylic acid solution by conducting the crystallization step, the adjustment step, the sweating step and the melting step in this order (hereinafter, processing from the crystallization step through the melting step may be referred to as a "crystallization operation").

In the crystallization step, a cooling medium cooled by a heat source device is supplied to a crystallizer. Any heat source device can be used as the heat source device used in the crystallization step, as long as the heat source device can cool the cooling medium. Examples of the heat source device include a multitubular heat exchanger using liquefied gas or steam as a heat source. Also, a refrigerator may be used as the heat source device that is capable of supplying both a cooling medium and a heating medium. As the refrigerator, an absorption refrigerator (e.g. ammonia absorption refrigerator, water-lithium bromide refrigerator, and the like), a compression refrigerator, an adsorption refrigerator and the like can be used.

The cooling medium is not particularly limited, as long as it is kept in a liquid state in the heat source device and the crystallizer. The cooling medium means a heat medium which has been cooled by the heat source device. The cooling medium may be the same as or different from the heating medium used in the sweating step or the melting step. Examples of the cooling medium include ethylene glycol aqueous solution, glycerin aqueous solution, methanol aqueous solution, and the like.

Temperature of the cooling medium discharged from the heat source device is not particularly limited, as long as it is lower than the solidification point of the crude (meth)acrylic acid solution. The solidification point of the crude (meth)acrylic acid solution varies depending on the impurity composition and the (meth)acrylic acid concentration thereof. For example, a crude acrylic acid solution containing 80 mass % to 95 mass % of acrylic acid and water as a most component of impurity generally has a solidification point of more than −5° C. and 13.5° C. or lower.

The temperature of the cooling medium discharged from the heat source device is preferably adjusted appropriately according to the solidification point of the (meth)acrylic acid solution fed to the crystallizer. For example, in the case of the solution containing 80 mass % to 95 mass % of acrylic acid, the temperature of the cooling medium is preferably −5° C. or lower, more preferably −10° C. or lower, and preferably −40° C. or higher, more preferably −30° C. or higher. As described above, the upper limit of the temperature of the cooling medium discharged from the heat source device is only needed to be lower than the solidification point of the crude (meth)acrylic acid solution; and the temperature of the cooling medium discharged from the heat source device is preferably −5° C. or lower in terms of efficient crystallization. Meanwhile, in the case where the temperature of the cooling medium discharged from the heat source device is lower than −40° C., it is likely that a heat source device with high-power specifications is needed or energy consumption of the heat source device is increased due to increase in the cooling load of the heat source device; and thus, the temperature of the cooling medium discharged from the heat source device is preferably −40° C. or higher.

In the crystallization step, the temperature of the cooling medium entering the crystallizer may be adjusted appropriately according to the progress of crystallization. Two or more kinds of cooling media that have different temperatures from each other may be used. For example, two kinds of cooling media, that is, a cooling medium whose temperature is in the range of −10° C. to −5° C. and a cooling medium whose temperature is in the range of −30° C. to −15° C., may be used. However, in the case where a small-scale crystallizer is employed, cooling medium having desired temperature is discharged from the heat source device and may be supplied to the crystallizer at that temperature.

Any crystallizer can be used as long as the crystallizer is capable of crystallizing the crude (meth)acrylic acid solution. The crystallizer preferably has a heat-transfer surface. In this case, it is preferred that the interior of the crystallizer is partitioned by the heat-transfer surface into a part which the cooling medium or the heating medium is supplied to (i.e. a heat medium-present part) and a part where the crude (meth) acrylic acid solution and/or the (meth)acrylic acid crystal is present (i.e. a crystal-present part).

As the crystallizer having a heat-transfer surface, an apparatus used as a heat exchanger generally can be employed, and particularly, an apparatus used as a heat exchanger in which heat is exchanged between liquids is preferably employed. For example, a plate-type heat exchanger comprising a single plate or a plurality of plates stacked at intervals, wherein the heat medium-present part(s) and the crystal-present part(s) are alternately disposed while being separated by the plate(s); a multitubular (shell-and-tube) heat exchanger comprising a plurality of tubes in a vessel, wherein heat is exchanged between the interiors and exteriors of the tubes; a double-pipe heat exchanger comprising an outer pipe and an inner pipe disposed in the outer pipe, wherein heat is exchanged between the interior and exterior of the inner pipe; or the like may be employed. Cross-sectional shapes of the tube of the multitubular heat exchanger and the pipe of the double-pipe heat exchanger are not particularly limited.

The crystallizer used in the producing process of the present invention is preferably capable of so-called dynamic crystallization by crystallizing the crude (meth)acrylic acid solution while having the (meth)acrylic acid solution flow downward in the form of a film (Falling Film method). In addition, the crystallizer is preferably capable of circulating a melt while having the melt flow downward in the form of a film (Falling Film method) to conduct melting. As such a crystallizer, a batch-type dynamic crystallization apparatus can be used. For example, a layer-crystallization apparatus of Sulzer Chemtech Ltd. of Switzerland, a crystallization apparatus disclosed in Japanese Examined Patent Application Publication No. 53-41637, or the like can be used.

In the crystallization step, the cooling medium is supplied to the crystallizer while the crude (meth)acrylic acid solution is supplied to the crystallizer. Thereby, the crude (meth)acrylic acid solution is cooled by the cooling medium to generate the (meth)acrylic acid crystal. In the crystallization step, it is preferred that the crude (meth)acrylic acid solution is circulated between the crystal-present part of the crystallizer and a circulation path interconnecting an inlet and an outlet of the crystal-present part to be crystallized, and as a result, crystallization can be performed efficiently.

No particular limitation is placed on the crude (meth)acrylic acid solution, and the crude (meth)acrylic acid solution can be any solution containing (meth)acrylic acid and an impurity thereof. Examples of the impurity include unreacted (meth)acrylic acid production raw materials, a collection liquid medium (e.g. water or the like), acetic acid, propionic acid, maleic acid, acetone, acrolein, furfural, formaldehyde and the like. The crude (meth)acrylic acid solution used in the producing process of the present invention preferably has (meth)acrylic acid concentration of 80 mass % or more, more preferably 90 mass % or more, and further preferably 95 mass % or more. When the (meth)acrylic acid concentration is 80 mass % or more, crystallization of the crude (meth)acrylic acid solution is facilitated. Meanwhile, the upper limit of the (meth)acrylic acid concentration is not particularly limited.

In the crystallization step, the cooling medium cooled by the heat source device is supplied to the crystallizer, the cooling medium is warmed by heat exchange with the crude (meth)acrylic acid solution, and the cooling medium is then discharged from the crystallizer. Thus, temperature of the cooling medium becomes higher at the outlet of the crystallizer than at the inlet of the crystallizer. In the crystallization step, (meth)acrylic acid is crystallized from the crude (meth)acrylic acid solution while maintaining impurities in the liquid state without causing crystallization as much as possible, thereby obtaining purified (meth)acrylic acid. Thus, the crude (meth)acrylic acid solution does not entirely crystallize in the crystallization step. Therefore, temperature of the cooling medium becomes higher at the outlet of the crystallizer than at the inlet of the crystallizer during the overall crystallization step. This means that the (meth)acrylic acid crystal generated within the crystallizer has a non-uniform temperature distribution in the crystallization step.

In the crystallization step, for example, the temperature of the cooling medium to be supplied to the crystallizer is controlled to gradually lower with the progress of crystallization and the crystallization step is terminated at the time when a predetermined amount of the crystal is obtained; alternatively, the temperature of the cooling medium to be supplied to the crystallizer is controlled so as to keep at a fixed low temperature. In the crystallization step, the final temperature difference of the cooling medium between the inlet and the outlet of the crystallizer typically becomes about 2° C. to 5° C.

In the crystallization step, the cooling medium which has been discharged from the crystallizer is returned to the heat source device to be cooled, and then, this cooling medium is supplied again to the crystallizer. In the crystallization step, it is preferred that the cooling medium whose temperature has risen by receiving heat at the crystallizer is cooled again by the heat source device, whereby the cooling medium is recycled.

The crude (meth)acrylic acid solution which remains uncrystallized in the crystallization step, that may be hereinafter referred to as a "residual mother liquid", is discharged from the system in the end of the crystallization step, in the adjustment step, or in the sweating step. When the residual mother liquid is discharged from the system in the sweating step, it is efficient that the residual mother liquid is discharged from the system together with the melted liquid generated in the sweating step.

For obtaining purified (meth)acrylic acid from a crude (meth)acrylic acid solution by crystallization, it is general that the sweating step is conducted directly after the crystallization step. Here, the sweating step means a step of melting a part of the (meth)acrylic crystal and discharging the generated melted liquid from the system. According to the sweating step, impurities present between the crystals or on the surface of the crystal are washed away, and hence, a more highly purified (meth)acrylic acid can be obtained in the subsequent melting step. However, as explained above, the (meth)acrylic acid crystal generated within the crystallizer in the crystallization step has a non-uniform temperature distribution. Specifically, temperature of the (meth)acrylic acid crystal is low at an inlet side of the cooling medium in the crystallizer, whereas temperature of the (meth)acrylic acid crystal is high at an outlet side of the cooling medium in the crystallizer. When the (meth)acrylic acid crystal has a non-uniform temperature distribution within the crystallizer like this, melting of the (meth)acrylic acid crystal is not performed uniformly and the (meth)acrylic acid crystal having higher temperature is preferentially melted if the sweating step is conducted directly after the crystallization step. As a result, the (meth)acrylic acid crystal with high purity comes to melt too much at a higher temperature part of the (meth)acrylic acid crystal, and on the contrary, impurities present between the crystals or on the surface of the crystal come to be not removed sufficiently at a lower temperature part of the (meth)acrylic acid crystal.

Therefore, in the producing process of the present invention, the adjustment step is provided for returning the cooling medium which has been discharged from the crystallizer to the crystallizer without cooling between the crystallization step and the sweating step. When the cooling medium discharged from the crystallizer is returned to the crystallizer without cooling, temperature of the cooling medium is made ideally uniform at the inlet of the crystallizer and the outlet of the crystallizer, whereby temperature of the cooling medium within the crystallizer is made uniform. This effect is thought to make temperature of the (meth)acrylic crystal within the crystallizer uniform. Therefore, in the sweating step following the adjustment step, the (meth)acrylic acid crystal is partially-melted uniformly without dependence on a crystallization location within the crystallizer, and it becomes possible to effectively remove impurities present between the crystals and on the surface of the crystal. As a result, purified (meth)acrylic acid with higher purity can be obtained in the melting step.

For returning the cooling medium discharged from the crystallizer to the crystallizer without cooling in the adjustment step, a shortcut interconnecting the outlet and the inlet of the crystallizer may be provided and the cooling medium discharged from the crystallizer may be returned to the crystallizer though the shortcut, for example. Alternatively, the cooling medium discharged from the crystallizer may pass through the heat source device in a non-operational state and then return to the crystallizer.

In the adjustment step, neither heating nor cooling are conducted actively, except for unavoidable transfer of heat from piping, pumps, or the like. Moreover, if there is an unavoidable transfer of heat, the amount of such heat transfer is preferably as small as possible. For example, in the case where the cooling medium discharged from the crystallizer is returned to the crystallizer after passing through the heat source device in a non-operational state, the cooling medium might be cooled by the heat source device due to residual cold, and therefore, the cooling medium discharge from the crystallizer is preferably returned to the crystallizer without passing through the heat source device.

In the adjustment step, temperature difference at between the inlet of the crystallizer and the outlet of the crystallizer is preferably made small. That is, temperature variation of the cooling medium after discharged from the crystallizer and until returned to the crystallizer is preferably made small. Specifically, the temperature variation is preferably within 1.0° C. and more preferably within 0.5° C. When the temperature variation is within 1.0° C., temperature of the cooling medium in the crystallizer becomes sufficiently uniform, and purified (meth)acrylic acid with high purity is easily obtained finally.

In order to make the temperature difference of the cooling medium between the outlet of the crystallizer and the inlet of the crystallizer small, the cooling medium discharged from the crystallizer is preferably returned to the crystallizer through a flow path that is as short as possible. Specifically, a shortcut interconnecting the outlet and the inlet of the crystallizer is preferably provided, and the cooling medium discharged from the crystallizer is preferably returned to the crystallizer through the shortcut. A pump may be provided in the shortcut for returning the cooling medium to the crystallizer, if needed.

The adjustment step preferably takes 1 minute or longer, and more preferably 2 minutes or longer. When the adjustment step takes 1 minute or longer, temperature of the cooling medium in the crystallizer is made sufficiently uniform, and further, heat exchange between the cooling medium and the (meth)acrylic acid crystal occurs in the crystallizer so that temperature of the (meth)acrylic acid crystal in the crystallizer can be readily made uniform. On the other hand, the adjustment step preferably takes 10 minutes or shorter, and more preferably 5 minutes or shorter. When the adjustment step takes more than 10 minutes, it is difficult to make temperature of the cooling medium or the (meth)acrylic acid crystal in the crystallizer further uniform, resulting in lowering productivity due to increase of time span of the adjustment step.

In the adjustment step, temperature of the cooling medium discharged from the crystallizer and returned to the crystallizer during the initial stage of the adjustment step is nearly equal to the temperature of the cooling medium discharged from the crystallizer at the end of the crystallization step; however, the temperature of the cooling medium generally tends to increase as the adjustment step proceeds due to transfer of heat from piping, pumps or the like to the cooling medium. In this case, the time span of the adjustment step is adjusted appropriately so that the temperature of the cooling medium stays within a range lower than the melting point of the (meth)acrylic acid crystal. Preferably, the temperature of the cooling medium discharged from the crystallizer and returned to the crystallizer is maintained in the temperature range that is at least 5° C. lower than the melting point of the (meth)acrylic acid crystal.

The adjustment step is followed by the sweating step. In the sweating step, a heating medium is supplied to the crystallizer to partially melt the (meth)acrylic acid crystal, thereby obtaining a melted liquid, and the melted liquid is discharged from the system.

The heating medium means a heat medium which has been heated by a heat source device. The heating medium is not particularly limited, as long as it is kept in a liquid state in a heat source device and the crystallizer. The above cited example heat source devices can be used as the heat source device, and a refrigerator can be also used as the heat source device. The example substances cited as the cooling medium can be used as the heating medium.

Temperature of the heating medium discharged from the heat source device is not particularly limited, as long as it exceeds the melting point of the (meth)acrylic acid crystal. The temperature of the heating medium discharged from the heat source device is preferably 15° C. or higher, more preferably 25° C. or higher, and preferably 45° C. or lower, more preferably 40° C. or lower. As described above, the lower limit of the temperature of the heating medium discharged from the heat source device is only needed to be higher than the melting point of the (meth)acrylic acid crystal; however, the temperature of the heating medium discharged from the heat source device is preferably 15° C. or higher in terms of efficient melting. Meanwhile, in the case where the temperature of the heating medium discharged from the heat source device is higher than 45° C., continuous operation of the crystallizer may become difficult or the purity or yield of the obtained (meth)acrylic acid may decline, due to occurrence of polymerization of (meth)acrylic acid in the crystallizer. In addition, it is likely that a heat source device with high-power specifications is needed or energy consumption of the heat source device is increased due to increase in the heating load of the heat source device. Therefore, the temperature of the heating medium discharged from the heat source device is preferably 45° C. or lower.

In the sweating step and the below-described melting step, temperature of the heating medium entering the crystallizer may be adjusted appropriately according to the progress of melting. Comparing the sweating step and the below-described melting step, it is preferred that the temperature of the heating medium entering the crystallizer in the melting step is higher than that in the sweating step.

In the sweating step, the heating medium is supplied to the crystallizer to heat the (meth)acrylic acid crystal, whereby a part of the (meth)acrylic acid crystal is melted. As a result, impurities present between the crystals or on the surface of the crystal of the (meth)acrylic acid crystal are removed, and purified (meth)acrylic acid with higher purity is obtained in the melting step following the sweating step.

In the sweating step, it is preferred that 1 mass % to 10 mass % of the (meth)acrylic acid crystal is melted. When such a portion of the (meth)acrylic acid crystal is melted, the purity and yield of the purified (meth)acrylic acid obtained in the melting step can be effectively enhanced.

The melted liquid obtained by partially-melting of the (meth)acrylic acid crystal is discharged from the system. The expression "discharged from the system" means discharge once from the crystallizer. The melted liquid discharged from the system may be used as a crude (meth)acrylic acid solution to be fed to another crystallization step; or, the melted liquid may be returned to any step preceding crystallization. Also, the residual mother liquid generated in the crystallization step and discharged from the system may be treated similarly to the melted liquid discharged from the system.

The sweating step is followed by the melting step. In the melting step, the heating medium is supplied to the crystallizer to melt the (meth)acrylic acid crystal, thereby obtaining purified (meth)acrylic acid. Examples of the heating medium used in the melting step are the same as the examples cited for the heating medium used in the sweating step, and it is efficient to use the same heating medium substance for the melting step as that for the sweating step. In the melting step, purified (meth)acrylic acid which is purer than the crude (meth)acrylic acid solution is obtained. According to the producing process of the present invention, purified (meth)acrylic acid with higher purity can be obtained by providing the adjustment step.

In the melting step, a melt that melts initially in association with the supply of the heating medium is preferably circulated between the crystal-present part of the crystallizer and a circulation path interconnecting an inlet and an outlet of the crystal-present part to promote melting of the remaining (meth)acrylic acid crystal. In addition, a polymerization inhibiter is preferably fed to the crystal-present part of the crystallizer in terms of prevention of polymerization of the (meth)acrylic acid.

In the case where the producing process of the present invention is a process for producing acrylic acid, it is preferred that the acrylic acid crystal is melted in the melting step so that temperature of the purified acrylic acid is in the range of 18° C. to 25° C. and temperature difference between the heating medium and the purified acrylic acid is in the range of 5° C. to 25° C. When the melting step is conducted in this manner, the acrylic acid crystal can be melted rapidly, resulting in improving productivity of acrylic acid.

Figure 1:
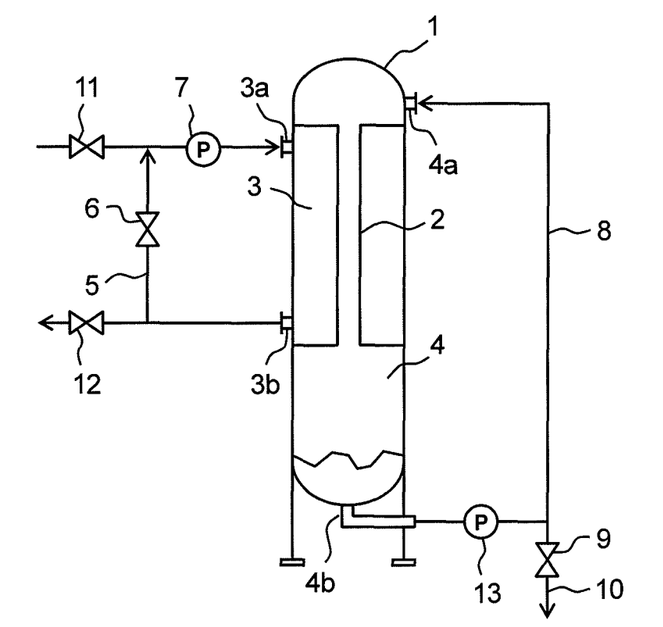
FIG. 1 shows an example of a crystallization apparatus used in the producing process of the present invention.

Measurement points of temperatures of the purified acrylic acid, which is obtained by melting the acrylic acid crystal, and the heating medium are explained referring to FIG. 1. FIG. 1 shows a crystallization apparatus usable in the producing process of the present invention. A crystallizer 1 is provided with a crystallization tube 2 functioning as a heat transfer surface. The interior and exterior faces of the crystallization tube 2 partition the crystallizer 1 into a heat medium-present part 3 supplied with the cooling medium or the heating medium and a crystal-present part 4 in which the crude (meth)acrylic acid solution and/or the (meth)acrylic acid crystal is present. The cooling medium and the heating medium are supplied to the heat medium-present part 3 of the crystallizer 1 through an inlet port 3a and discharged from the crystallizer 1 through an outlet port 3b. The crystallizer 1 is also provided with a circulation path 8 for circulating the crude (meth)acrylic acid solution and/or the purified (meth)acrylic acid through the crystallizer 1, and the circulation path 8 is equipped with a circulation pump 13.

The temperature of the purified acrylic acid means temperature of the purified acrylic acid flowing through the circulation path 8, and concretely, the temperature of the purified acrylic acid is measured by a thermometer installed between an outlet port 4b of the crystallizer 1 and the circulation pump 13. The temperature of the heating medium means temperature of the heating medium flowing through a flow path for leading the heating medium to the crystallizer 1 (a flow path connecting to the inlet port 3a), and concretely, the temperature of the heating medium is measured by a thermometer installed near the inlet port 3a of the crystallizer 1. The temperature of the purified acrylic acid can be adjusted in a desired temperature range by controlling the temperature of the heating medium. Accordingly, adjustments of the temperature of the purified acrylic acid and the temperature difference between the heating medium and the purified acrylic acid to the range of 18° C. to 25° C. and 5° C. to 25° C., respectively, can be accomplished by properly controlling the temperature of the heating medium.

If the temperature of the purified acrylic acid obtained by melting the acrylic acid crystal is lower than 18° C., melting speed becomes slow, and as a result, it takes a long time to terminate the melting and productivity of acrylic acid is lowered. Further, in melting in the Falling Film method, pressure is increased in the crystallization tube, and the apparatus may be ceased in the worst case. On the other hand, in the case where the temperature of the purified acrylic acid obtained by melting the acrylic acid crystal exceeds 25° C., it takes a long time until the temperature of the purified acrylic acid exceeds 25° C., resulting in lowering the productivity.

If the temperature difference between the heating medium and the purified acrylic acid obtained by melting the acrylic acid crystal is less than 5° C. or becomes less than 5° C. during the melting, the melting speed becomes slow, and as a result, it takes a long time to terminate the melting and productivity of acrylic acid is lowered. Further, in melting by the Falling Film method, pressure is increased in the crystallization tube, and the apparatus may be ceased in the worst case. On the other hand, if the temperature difference between the heating medium and the purified acrylic acid obtained by melting the acrylic acid crystal is more than 25° C. or becomes more than 25° C. during the melting, polymerization of acrylic acid easily occurs.

In the melting step, it is preferred that the acrylic acid crystal is melted while being wetted with the purified acrylic acid obtained by melting the acrylic acid crystal. For example, the purified acrylic acid is preferably circulated through the crystallizer to melt the acrylic acid crystal. When the acrylic acid crystal is melted in this manner, the acrylic acid crystal can be more efficiently melted.

In the producing process of the present invention, processing may be performed by conducting the series of the crystallization step, adjustment step, sweating step and melting step in this order multiple times. In this case, the purified (meth)acrylic acid obtained in the melting step is supplied again to the crystallization step as a crude (meth)acrylic acid solution. Repeating the crystallization operation from the crystallization step through the melting step multiple times enables to obtain purified (meth)acrylic acid with higher purity. Preferably, the crystallization operation is repeated 3 to 5 times.

The producing process of the present invention may also be performed by parallel conducting the crystallization operations using a plurality of crystallizers. For example, assuming the use of two crystallizers, it is preferred that while the crystallization step or the adjustment step is conducted in one crystallizer, the sweating step or the melting step is conducted in the other crystallizer. In this case, the cooling medium is supplied to one crystallizer and the heating medium is supplied to the other crystallizer, and hence, using a refrigerator as the heat source device that is capable of supplying both the cooling medium and the heating medium is efficient since both heat and cold generated by the refrigerator are utilized in any step of respective crystallization operations.

The process for producing (meth)acrylic acid of the present invention preferably further comprises the step of obtaining the crude (meth)acrylic acid solution. The step of obtaining the crude (meth)acrylic acid solution preferably has a gas-phase catalytic oxidation step of producing (meth)acrylic acid-containing gas from a (meth)acrylic acid production raw material by gas-phase catalytic oxidation and a collection step of collecting the (meth)acrylic acid-containing gas with a liquid medium. Also, the step of obtaining the crude (meth) acrylic acid solution may has a condensation step of condensing the (meth)acrylic acid-containing gas instead of the collection step. Further, for the purpose of increasing (meth) acrylic acid content in the (meth)acrylic acid solution obtained in the collection step or the condensation step, a purification step such as, for example, a distilling purification step may be provided after the collection step or the condensation step. The process for producing (meth)acrylic acid of the present invention can be suitably conducted by using the crude (meth)acrylic acid solution obtained from the foregoing step of obtaining the crude (meth)acrylic acid solution.

In the gas-phase catalytic oxidation step, propane, propylene, (meth)acrolein, isobutylene, or the like is used as the (meth)acrylic acid production raw material, and the (meth) acrylic acid production raw material undergoes gas-phase catalytic oxidation by molecular oxygen to produce the (meth)acrylic acid-containing gas. The gas-phase catalytic oxidation is preferably carried out using a conventionally-known oxidation catalyst.

In the collection step, the (meth)acrylic acid-containing gas obtained in the gas-phase catalytic oxidation step is collected with a liquid medium in a collection column to obtain the (meth)acrylic acid solution. Examples of the liquid medium include water, (meth)acrylic acid-containing water, a high boiling point solvent (e.g. diphenyl ether, biphenyl and the like), and the like. In the present invention, the (meth) acrylic acid solution obtained in the collection step may be supplied to the crystallization step as the crude (meth)acrylic acid solution. Also, the (meth)acrylic acid solution obtained by condensing the (meth)acrylic acid-containing gas may be supplied to the crystallization step as the crude (meth)acrylic acid solution.

Next, an example embodiment of the producing process of the present invention is explained referring to FIG. 1. However, the present invention is not limited to the embodiment shown in the drawing.

A crystallizer 1 is provided with a crystallization tube 2 functioning as a heat transfer surface. The interior and exterior faces of the crystallization tube 2 partition the crystallizer 1 into a heat medium-present part 3 supplied with the cooling medium or the heating medium and a crystal-present part 4 in which the crude (meth)acrylic acid solution and/or the (meth) acrylic acid crystal is present.

In the crystallization step, the cooling medium cooled by a heat source device is supplied to the heat medium-present part 3 of the crystallizer 1 through an inlet port 3a, and the cooling medium introduced into the crystallizer 1 is discharged from the crystallizer 1 through an outlet port 3b. In the crystallization step, valves 11 and 12 in a heat medium line are opened, and the heat medium entering the inlet port 3a is adjusted to a desired temperature by opening or closing of a valve 6 provided in a shortcut 5 interconnecting the inlet port 3a and the outlet port 3b of the crystallizer 1. However, in the case where a small-scale crystallizer is employed, and cooling medium having a desired temperature is discharged from the heat source device and supplied to the crystallizer at that temperature, the valve 6 may be closed in the crystallization step. A crude (meth)acrylic acid solution is fed to the crystal-present part 4 of the crystallizer 1 through an inlet port 4a in a predetermined amount and cooled within the crystallization tube 2, whereby a (meth) acrylic acid crystal is generated on the inner surface of the crystallization tube 2. The crude (meth)acrylic acid solution that had not crystallized within the crystallization tube 2 and flowed downward to the lower part of the crystallizer 1 is fed again to the crystallizer 1 through a circulation path 8 interconnecting the outlet port 4b and the inlet port 4a by a circulation pump 13. The crude (meth)acrylic acid solution that had remained without crystallizing in the crystallization step is collected at the bottom of the crystallizer 1 as a residual mother liquid. In the crystallization step and the adjustment step, a valve 9 in a flow path 10 is closed.

In the adjustment step, the valves 11 and 12 in the heat medium line are closed, the valve 6 in the shortcut 5 is opened, and the cooling medium discharged from the crystallizer 1 through the outlet port 3b is returned to the crystallizer 1 by a pump 7 via the shortcut 5. Since any cooling means such as a heat source device is not provided in the flow path extending from the outlet port 3b of the crystallizer 1 to the inlet port 3a of the crystallizer 1, the cooling medium comes to be returned to the crystallizer 1 without cooling. Temperatures of the cooling medium at the inlet port 3a and the outlet port 3b of the crystallizer 1 are made uniform due to the adjustment step, and as a result, temperature of the (meth)acrylic acid crystal generated on the inner surface of the crystallization tube 2 is made uniform.

In the sweating step, the valves 11 and 12 in the heat medium line are opened, the heating medium is supplied to the heat medium-present part 3 of the crystallizer 1 to melt a part of the (meth)acrylic acid crystal deposited on the inner surface of the crystallization tube 2. In the sweating step and the melting step, the valve 6 provided in the shortcut 5 is closed. In the sweating step, the valve 9 in the flow path 10 is opened, and the (meth)acrylic acid melt generated in the sweating step is discharged from the system through the flow path 10 together with the residual mother liquid.

In the melting step, the heating medium is supplied to the heat medium-present part 3 of the crystallizer 1 to melt the (meth)acrylic acid crystal deposited on the inner surface of the crystallization tube 2, thereby obtaining purified (meth) acrylic acid. The purified (meth)acrylic acid is withdrawn from the lower part (bottom) of the crystallizer 1, returned to the top of the crystallizer 1 through the circulation path 8 by the circulation pump 13, and then made to flow downward on the surface of the (meth)acrylic acid crystal. Thus, the purified (meth)acrylic acid that has been circulated flows downward while wetting the (meth)acrylic acid crystal to promote melting the (meth)acrylic acid crystal. Therefore, supplying the purified (meth)acrylic acid again to the crystallizer 1 through the circulation path 8 enables efficient melting of the (meth)acrylic acid crystal. The obtained purified (meth) acrylic acid is discharged through the flow path 10 and is recovered by opening the valve 9 in the flow path 10.

EXAMPLES

The present invention is hereinafter described more specifically by reference to Examples; however, the scope of the present invention is not limited to these Examples.

Example 1

Reaction gas obtained by gas-phase catalytic reaction of propylene was introduced into a collection column and made to contact with an aqueous solution for collecting. A crude acrylic acid solution consisting of 90.0 mass % of acrylic acid, 3.2 mass % of water, 1.9 mass % of acetic acid, 0.6 mass % of maleic acid, 1.5 mass % of acrylic acid dimer, 0.07 mass % of furfural, 0.27 mass % of benzaldehyde, 0.06 mass % of formaldehyde, 0.1 mass % of hydroquinone, and 2.3 mass % of other impurities was recovered from the bottom of the collection column. The preparation of the crude acrylic acid solution was conducted in the same manner as Example 1 of Japanese Unexamined Laid-open Patent Application Publication No. 2005-15478. Temperature of the crude acrylic acid solution recovered from the collection column was 91° C.

The obtained crude acrylic acid solution was cooled and then subjected to the crystallization operation. The crystallizer was provided with three metallic crystallization tubes, each of which had a length of 6 m and an inner diameter of 70 mm, at an upper part of the crystallizer, had a double jacket structure capable of cooling and heating from the external of the crystallization tube, and was provided with a reservoir at a lower part of the crystallizer. The crystallizer had such mechanisms that a liquid in the reservoir was able to be transferred to upper parts of the tubes by a circulation pump and made to flow downward on the inner surfaces of the tubes in the form of falling film. The jacket was controlled so as to keep a constant temperature by a thermostat.

In the crystallization step, a cooling medium cooled by a heat source device was supplied to the exterior of the crystallization tube while the crude acrylic acid solution was fed to the interior of the crystallization tube from the upper part of the crystallization tube. The crude acrylic acid solution was made to flow downward as a film form on the inner surfaces of the crystallization tube to generate acrylic acid crystal on the inner surface of the crystallization tube. The cooling medium was circulated between the heat source device and the crystallizer. As the crystallization progressed, temperature of the cooling medium was adjusted to lower, and the crystallization step was completed when a predetermined amount of the acrylic acid crystal was generated. In the crystallization step, the temperature of the cooling medium was lowered to −15° C. finally, and the final temperature difference of the cooling medium at between the inlet port and the outlet port of the crystallizer was about 5° C.

In the subsequent adjustment step, cooling of the cooling medium by the heat source device was stopped; and supplying of the cooling medium to the crystallizer was continued. As a result, the temperature difference of the cooling medium at between the inlet port and the outlet port of the crystallizer became within 0.2° C. The adjustment step took 5 minutes.

In the subsequent sweating step, heating medium was supplied to the crystallizer. Temperature of the heating medium entering the crystallizer was adjusted such that the temperature at the outlet port of the crystallizer became about the melting point of the acrylic acid crystal. In the sweating step, about 2 mass % to 5 mass % of the acrylic acid crystal melted, and the obtained melted liquid was discharged from the crystallizer together with the residual mother liquid generated in the crystallization step.

In the subsequent melting step, heating medium at 37° C. was supplied to the crystallizer to completely melt the acrylic acid crystal, thereby obtaining purified acrylic acid. At this time, the purified acrylic acid was withdrawn from the lower part of the crystallizer, and then returned to the upper part of the crystallization tube to be circulated.

The purified acrylic acid obtained in the melting step was subjected again to the crystallization step as a crude acrylic acid solution, and further subjected to the second round of the crystallization operation of the adjusting step, the sweating step and the melting step. The third and fourth rounds of the crystallization operation were conducted in the same manner. In the melting steps of the third and fourth rounds, an acrylic acid solution containing 5 mass % of p-methoxyphenol was added as a polymerization inhibitor.

The purified acrylic acid obtained from the forth round of the crystallization operation contained 99.94 mass % of acrylic acid along with 85 ppm by mass of water, 420 ppm by mass of acetic acid, 2 ppm by mass of maleic acid, 0.2 ppm by mass of furfural, 0.1 ppm by mass of benzaldehyde, 0.0 ppm by mass of formaldehyde and 47 ppm by mass of acrylic acid dimer.

Comparative Example 1

Purified acrylic acid was obtained by conducting the same operations as in Example 1, except that the adjustment step was not conducted. Purified acrylic acid obtained from the forth round of the crystallization operation contained 99.92 mass % of acrylic acid along with 123 ppm by mass of water, 530 ppm by mass of acetic acid, 3 ppm by mass of maleic acid, 0.2 ppm by mass of furfural, 0.2 ppm by mass of benzaldehyde, 0.0 ppm by mass of formaldehyde and 85 ppm by mass of acrylic acid dimer. The content of impurities in the purified acrylic acid obtained in Comparative Example 1 was higher than that in the purified acrylic acid obtained in Example 1.

Example 2

The crude acrylic acid solution obtained in Example 1 was subjected to the crystallization operation in which the crystallizer used in Example 1 was used. In the crystallization operation, the crystallization step, the sweating step and the melting step (dynamic crystallization) were performed as follows. In the crystallization step, the crude acrylic acid solution was fed to the reservoir and made to flow downward as a film form on the surface of the crystallization tube by the circulation pump while lowering the temperature of the jacket to the solidification point or lower of the crude acrylic acid solution, whereby about 60 mass % to 90 mass % of the crude acrylic acid solution was crystallized on the surface of the tube. In the sweating step, the circulation pump was brought to a stop, and the temperature of the jacket was raised to about the solidification point of the acrylic acid crystal so that about 2 mass % to 5 mass % of the acrylic acid crystal sweated. After sweating, the obtained melted liquid was pumped out together with the residual mother liquid generated in the crystallization step. In the melting step, the temperature of the jacket was raised to the solidification point or higher of the acrylic acid crystal to melt the acrylic acid crystal, and the obtained purified acrylic acid was pumped out. After starting the melting, the purified acrylic acid was circulated to the upper part of the apparatus and made to flow downward on the acrylic acid crystal.

The purified acrylic acid obtained in the melting step was subjected again to the crystallization step as a crude acrylic acid solution, and further subjected to the second round of the crystallization operation of the sweating step and the melting step. The third and fourth rounds of the crystallization operation were conducted in the same manner.

In the respective melting steps during the first to fourth rounds of the crystallization operation, the temperatures of the heating medium were adjusted to 37° C. In the melting step of the first round of the crystallization operation, the temperature of the melt (purified acrylic acid) was 12° C. at the beginning of the circulation, and thereafter, the temperature of the melt (purified acrylic acid) circulating was gradually elevated to 20° C., and at that point, the melting operation was stopped. In the melting steps of the second or more rounds of the crystallization operation, since the solidification points of the acrylic acid crystals became different from that in the melting step of the first round of the crystallization operation, the melting in the second or more rounds was started at the temperature of 0° C. to 1.5° C. higher than the temperature (12° C.) of the melt (purified acrylic acid) in melting step of the first round and the temperature of the melt was gradually risen to 20° C., and at that point, the melting operation was stopped. Thus, in the first to fourth rounds of the crystallization operation, the temperatures of the melts (purified acrylic acid) were in the range of 12° C. to 20° C. and the temperature differences between the heating medium and the melts (purified acrylic acid) were in the range of 17° C. to 25° C.

After repeating the crystallization operation four times, purified acrylic acid having a purity of 99.94 mass % was obtained at 3.30 kg/h. No polymer was observed in the obtained purified acrylic acid. The obtained purified acrylic acid further contained 100 ppm by mass of water, 450 ppm by mass of acetic acid, 3 ppm by mass of maleic acid, 0.4 ppm by mass of furfural, 0.1 ppm by mass of benzaldehyde, 0.0 ppm by mass of formaldehyde, and 30 ppm by mass of acrylic acid dimer, as other components. Purification yield of acrylic acid was 99.0%.

Comparative Example 2

Production of acrylic acid was conducted in the same manner as in Example 2, except that the temperature of the heating medium was adjusted to 39° C. in the melting step and the whole acrylic acid crystal was melted by circulating the melt (purified acrylic acid) by the circulation pump so that the temperature of the melt (purified acrylic acid) reached 28° C. In the melting step, the temperature difference between the heating medium and the melt (purified acrylic acid) sometimes exceeded 30° C. at a maximum. As a result, purified acrylic acid having a purity of 99.91 mass % was obtained at 3.09 kg/h. In the obtained purified acrylic acid, a small amount of polymers was observed.

Comparative Example 3

Production of acrylic acid was conducted in the same manner as in Example 2, except that the whole acrylic acid crystal was melted by circulating the melt (purified acrylic acid) by the circulation pump so that the temperature of the melt (purified acrylic acid) reached 17° C. in the melting step. In this case, when the temperature of the melt (purified acrylic acid) reached 17° C., the acrylic acid crystal still remained, and therefore, it was needed to continue circulation of the melt (purified acrylic acid) of 17° C. As a result, purified acrylic acid having a purity of 99.94 mass % was obtained at 2.35 kg/h. No polymer was observed in the obtained purified acrylic acid. The temperature difference between the heating medium and the melt (purified acrylic acid) was in the range of 5° C. to 25° C.

Comparative Example 4

Production of acrylic acid was conducted in the same manner as in Example 2, except that the whole acrylic acid crystal was melted by circulating the melt (purified acrylic acid) by the circulation pump so that the temperature of the melt (purified acrylic acid) reached 28° C. in the melting step. As a result, purified acrylic acid having a purity of 99.94 mass % was obtained at 2.91 kg/h. No polymer was observed in the obtained purified acrylic acid. The temperature difference between the heating medium and the melt (purified acrylic acid) was in the range of 5° C. to 25° C.

Comparative Example 5

Production of acrylic acid was conducted in the same manner as in Example 2, except that the temperature of the heating medium was controlled so as to keep the temperature difference between the heating medium and the melt (purified acrylic acid) constantly within 2° C. in the melting step. Thus, the temperature of the heating medium was controlled in the range of 14° C. to 22° C. in the melting step of the first round. In this condition, the melt (purified acrylic acid) was circulated continuously until the whole acrylic acid crystal was melted. As a result, purified acrylic acid having a purity of 99.94 mass % was obtained at 2.46 kg/h. No polymer was observed in the obtained purified acrylic acid.

The temperature of the melt (purified acrylic acid), the temperature difference between the heating medium and the melt (purified acrylic acid), production amount (an amount of the purified acrylic acid per unit time), and presence or absence of polymers in the purified acrylic acid in Example 2 and Comparative Examples 2 to 5 are collectively shown in Table 1.

TABLE 1

| | Temperature of melt (° C.) | Temperature difference between heating medium and melt | Production amount (kg/h) | Presence or absence of polymer |
|---|---|---|---|---|
| Example 2 | 12 to 20 | Changing between 5° C. and 25° C. | 3.30 | Absence |
| Comparative Example 2 | 12 to 28 | Sometimes exceeding 30° C. | 3.09 | Presence |
| Comparative Example 3 | 12 to 17 | Changing between 5° C. and 25° C. | 2.35 | Absence |
| Comparative Example 4 | 12 to 28 | Changing between 5° C. and 25° C. | 2.91 | Absence |
| Comparative Example 5 | 12 to 20 | Constantly within 2° C. | 2.46 | Absence |

EXPLANATION OF REFERENCE

1: crystallizer
2: crystallization tube
3: heat medium-present part
4: crystal-present part
5: shortcut
8: circulation path

The invention claimed is:

1. A process for producing (meth)acrylic acid, comprising the steps in the following order:
   a crystallization step of supplying a cooling medium cooled by a heat source device to a crystallizer to obtain a (meth)acrylic acid crystal from a crude (meth)acrylic acid solution;
   an adjustment step of returning the cooling medium discharged from the crystallizer to the crystallizer without cooling the cooling medium, wherein the adjustment step is performed without further crystallization;
   a sweating step of supplying a heating medium to the crystallizer to partially melt the (meth)acrylic acid crystal, thereby obtaining a melted liquid, and discharging the melted liquid from the crystallizer; and
   a melting step of supplying the heating medium to the crystallizer to melt the (meth)acrylic acid crystal, thereby obtaining purified (meth)acrylic acid.

2. The process for producing (meth)acrylic acid according to claim 1, wherein the cooling medium discharged from the crystallizer is returned to the crystallizer without passing through the heat source device in the adjustment step.

3. The process for producing (meth)acrylic acid according to claim 1, wherein the adjustment step takes 1 minute or longer and 10 minutes or shorter.

4. The process for producing (meth)acrylic acid according to claim 1, wherein a temperature variation of the cooling medium after discharged from the crystallizer and until returned to the crystallizer is within 1.0° C. in the adjustment step.

5. The process according to claim 1, wherein
the process is a process for producing acrylic acid, and
an acrylic acid crystal is melted in the melting step so that a temperature of a purified acrylic acid is in a range of 18° C. to 25° C. and a temperature difference between the heating medium and the purified acrylic acid is in a range of 5° C. to 25° C.

6. The process for producing acrylic acid according to claim 5, wherein the acrylic acid crystal is melted while being wetted with the purified acrylic acid.

7. The process for producing acrylic acid according to claim 5, wherein the purified acrylic acid is circulated through the crystallizer to melt the acrylic acid crystal.

8. The process for producing (meth)acrylic acid according to claim 2, wherein the adjustment step takes 1 minute or longer and 10 minutes or shorter.

9. The process for producing (meth)acrylic acid according to claim 2, wherein a temperature variation of the cooling medium after discharged from the crystallizer and until returned to the crystallizer is within 1.0° C. in the adjustment step.

10. The process for producing (meth)acrylic acid according to claim 3, wherein a temperature variation of the cooling medium after discharged from the crystallizer and until returned to the crystallizer is within 1.0° C. in the adjustment step.

11. The process according to claim 2, wherein
the process is a process for producing acrylic acid, and
an acrylic acid crystal is melted in the melting step so that a temperature of a purified acrylic acid is in a range of 18° C. to 25° C. and a temperature difference between the heating medium and the purified acrylic acid is in a range of 5° C. to 25° C.

12. The process according to claim 3, wherein
the process is a process for producing acrylic acid, and
an acrylic acid crystal is melted in the melting step so that a temperature of a purified acrylic acid is in a range of 18° C. to 25° C. and a temperature difference between the heating medium and the purified acrylic acid is in a range of 5° C. to 25° C.

13. The process for producing acrylic acid according to claim 4, wherein
the process is a process for producing acrylic acid, and
an acrylic acid crystal is melted in the melting step so that a temperature of a purified acrylic acid is in a range of 18° C. to 25° C. and a temperature difference between the heating medium and the purified acrylic acid is in a range of 5° C. to 25° C.

14. The process according to claim 6, wherein the purified acrylic acid is circulated through the crystallizer to melt the acrylic acid crystal.

15. The process according to claim 1, wherein the crystallizer is a batch-type crystallizer.

16. The process according to claim 1, wherein the adjustment step takes 1 minute or longer.

17. The process according to claim 1, wherein the temperature of the cooling medium is adjusted lower than a melting point of the (meth)acrylic acid crystal in the adjustment step.

18. The process according to claim 1, further comprising the step of obtaining the crude (meth)acrylic acid by collecting (meth)acrylic acid-containing gas with a liquid medium or condensing (meth)acrylic acid-containing gas, followed by cooling the crude (meth)acrylic acid to be subjected to the crystallization step.

19. The process according to claim 1, wherein the cooling medium discharged from the crystallizer is returned to the crystallizer through a shortcut interconnecting an outlet of the crystallizer and an inlet of the crystallizer in the adjustment step.

* * * * *